United States Patent [19]

Ronay et al.

[11] Patent Number: 5,055,038
[45] Date of Patent: Oct. 8, 1991

[54] METHOD AND APPARATUS FOR MAKING AN ORTHODONTIC APPLIANCE

[75] Inventors: Franz Ronay, Rudolfsplatz 14, A-1010 Wien; Georg Ronay, Vienna, both of Austria

[73] Assignee: Ronay Franz, Vienna

[21] Appl. No.: 359,480

[22] Filed: May 31, 1989

[30] Foreign Application Priority Data

May 31, 1988 [AT] Austria ............................ 1419/88

[51] Int. Cl.$^5$ .............................................. A61C 3/00
[52] U.S. Cl. ...................................................... 433/24
[58] Field of Search ........................ 433/2, 18, 22, 24

[56] References Cited

U.S. PATENT DOCUMENTS 3,949,478  4/1977  Schinhammer ...................... 433/24
4,183,141  1/1980  Dellinger et al. .................... 433/24
4,431,409  2/1984  Picard .................................... 433/2

Primary Examiner—John J. Wilson
Assistant Examiner—Cindy A. Cherichetti
Attorney, Agent, or Firm—Herbert Dubno; Andrew Wilford

[57] ABSTRACT

The process for making an orthodontic appliance comprises making an occlusal model of the patient's current dental arch, making an idealized dental arch model by positioning correctly tooth replicas, providing bracket supports guided on a guide device, setting the brackets in position on the tooth replicas by bracket supports so that the bottoms of the openings of the brackets next to each other lie along a line which follows an idealized course for the orthodontic arch wire, then making at least one negative extending over at least one tooth replica from a hardenable material and combining the negative with a reference element projecting from each of the bracket supports to form a reference unit for a tooth replica, removing the reference units from the guide device, filling intervening spaces resulting from the positioning the brackets, setting the reference units with a hardenable compensating mass on the tooth replicas, installing the reference units on the dental arch, adjusting the position of the brackets with the bracket supports, fixing the brackets, removing the reference units and installing the orthodontic arch wire. An apparatus for carrying out this process is also described.

24 Claims, 2 Drawing Sheets

METHOD AND APPARATUS FOR MAKING AN ORTHODONTIC APPLIANCE

FIELD OF THE INVENTION

Our present invention relates to a process for making an orthodontic appliance for correcting the position of the teeth of a patient and also to an apparatus for carrying out that process.

More particularly, the invention relates to a method of making an orthodontic appliance which corrects the position of the teeth of a patient. This orthodontic appliance comprises a plurality of brackets having openings and associated to the individual teeth and an orthodontic arch wire attachable to them.

A characteristic occlusal model is made of the patient's dental arch which is divided into a plurality of individual tooth replicas. An idealized model of the dental arch is made by arranging of the individual tooth replicas into their corrected positions which represents the aim of the orthodontic treatment. A guide device and the dental arch model are held fixed in relation to each other during the procedure.

BACKGROUND OF THE INVENTION

In making an orthodontic appliance it is required that the brackets be harmonized with the dental arch of the individual patient and simultaneously made in clearly defined positions Thus it is known from U.S. Pat. No. 3,477,128 to use brackets for this orthodontic appliance whose constructions are harmonized with the average anatomical shape and position of the individual tooth in a dental arch so that the number of required bends of the orthodontic arch wire used is substantially reduced, although the bends can never be completely eliminated.

Other known processes for additional individualizing of the brackets and thus for individual minimizing of the required wire bending require in part great expense, are connected with expensive manipulations requiring a high dexterity or leave the accuracy of the required manipulations to what can be determined by eye.

In the process as described in the U.S. Pat. No. 4,014,096 the bracket openings are cut individually which is rather costly.

In U.S. Pat. No. 4,160,322 a process of the above-described type for individualization of the brackets is disclosed, in which the brackets are held directly on the idealized model of the dental arch by a template. The template is curved according to the orthodontic arch wire curvature. A casting of the replica of the idealized model is made. This has the disadvantage that the process on the one hand is not suitable for setting brackets, which are characterized as "molar-tubes", which must be used for molars and on the other hand the casting acting for transfer of the brackets from the idealized model to the patient teeth can grip or embrace the brackets in the vicinity of the template only very loosely and with weak retention for want of working room.

A process and apparatus of the above-described kind is also known from U.S. Pat. No. 3,949,478. However the process requires a great deal of skill and precision of measurement by eye and the process requires a very complicated apparatus for positioning.

The European Patent Application Publication 0 084 443, discloses a process and an apparatus of the above-described kind in which, before the casting of the patient's dental arch, orienting structures are provided at the positions where the attachment is to be made on the patient's dental arch by adhesive material or platelets which are glued on.

The orienting structures serve for later positioning and attachment of the individualized brackets at the bases.

The individualization of the brackets is effected by lining the bases of the brackets, which are held on the tooth replicas of the idealized model by an orthodontic arch wire fixed by a retainer or holder. A disadvantage of this process is that for three-dimensional arrangement of the brackets on the patient's dental arch a structure in the vicinity of the attachment positions of the brackets is used which can be lost during the orthodontic treatment so that no reproducibility is possible.

Another disadvantage is that on individual lining of the bracket bases, the idealized model is pushed on the brackets held by the wire, so that the process is unsuitable for a jaw shape in which the dental arch curvature in the vicinity of the second molar is of equal width or smaller than that in the vicinity of the first molar Finally a process and apparatus for carrying out that process are known from U.S. Pat. No. 4,183,141, in which a bracket can be positioned on the tooth at a certain position by a bracket support. The bracket is pressed on the tooth or on the tooth replica by a pushing device, whereby the tooth surface forms a stop for the bracket during the pressing motion.

The disadvantage of this apparatus is that the direct contact of the bracket on the tooth surface determines the position of the slot-like bracket openings tangential to the tooth surface so that no compensation is effected for different tooth thicknesses and rotation requirements and numerous bends and angulations are required of the orthodontic arch wire fitted in the bracket openings.

OBJECTS OF THE INVENTION

It is an object of our invention to provide a process and apparatus for making a dental appliance which has none of the abovementioned disadvantages and difficulties.

It is also an object of our invention to provide a process and apparatus for making a dental appliance which requires less work to make but produces a precise individualized orthodontic appliance which can be attached to a patient's teeth exactly by an orthodontist and which fits the individual tooth curvatures of the patient.

It is another object of our invention to provide a process and apparatus for making a dental appliance which not only requires less work to make but on loss of brackets the individualization of the replacement brackets and their positioning on the teeth can be performed quickly and reproducibly.

It is an additional object of our invention to reduce the storage of a large number of different bracket types, including the so-called "molar tubes".

SUMMARY OF THE INVENTION

These objects and others which will become more readily apparent hereinafter are attained in accordance with our invention in a method of making an individualized orthodontic appliance.

According to the process of our invention bracket supports guided on the guide device are provided for each bracket related to the teeth replicas, the brackets are adjusted to their desired position in relation to the associated tooth replica by the bracket supports so that the bases of the openings of the brackets next to each other lie along a line which forms an at least segmentwise continuously running curve which follows the idealized course of the edge of the orthodontic arch wire adjacent the teeth. In the region of the incisal edges and/or the occlusal surfaces of the tooth replica at least one negative extending over at least one tooth replica, which covers at least a portion of the crown of the replica, is made from a hardenable material and a reference element projecting from the bracket support is connected with the negative.

The reference element, the negative, the bracket and the bracket support form a reference unit of the tooth replica and are released from the guide device.

If necessary the negative is divided into segments associated with a tooth replica. If required the surfaces of the brackets correlated with the tooth surfaces are provided with a hardenable compensating mass for filling of the intervening space resulting from the position of the brackets and the reference unit with the hardenable compensating mass is again set on the tooth replica for casting. Then the reference unit is installed on the appropriate tooth of the patient, each bracket is fixed on the patient's tooth and the reference unit is removed without the bracket. Then finally the orthodontic arch wire is installed in the bracket openings.

By the process according to our invention the occlusal fine adjustment by the orthodontist determined from the idealized model can be performed with an absolute minimum of required bending operations of the orthodontic arch wire or in segments and with a great saving of time. Furthermore the function of the fine adjustment, which thus far has been reserved for a removable device known as a gnathologic positioner, which is used after orthodontic treatment with fixed appliances, can be performed already during the treatment with fixed appliances by the individualized brackets according to our invention.

Advantageously the intervening space filling is effected by injection with a compensating mass.

For simplicity it is advantageous when the negative for all replicas in the idealized dental arch model is made in a single piece.

Advantageously the brackets are positioned by the bracket supports prior to their attachment to the patient's dental arch.

When a first layer of hardenable material is applied to the replica for making the negative, the reference element can be bonded by a second layer on the negative applied over the first layer so that both an optimum casting and also a simple connection of the reference element and the negative are obtainable.

Advantageously the fixing of the bracket to the tooth is effected by adhesive. If required, in this case the adhesive mass forms the compensating mass.

The process according to our invention is performable with an apparatus which has a securable guide device with a plurality of bracket supports mounted movably on it. The guide device comprises a guide for the bracket supports which is at least approximately parallel to the idealized course or path of the orthodontic arch wire, the guide being formed to receive the bracket supports The bracket support on the guide is combined with a reference element and the associated bracket. A simple radial alignment of the bracket support on the tooth replica is obtainable because of the special arrangement of the course of the orthodontic arch wire and the guide device; the individual bracket supports are closely spaced along the length of the guide device. Further the reference element and the bracket support are adjustable in their position relative to each other.

According to an advantageous feature of our invention the guide is formed from a rail on which the bracket supports are mounted slidably.

Advantageously the bracket support has a cylindrical projection by which it is slidable into the guide or on the rail and an additional protruding member spaced from the cylindrical projection, whose spacing corresponds to the spacing between the wall of the guide and the edge of the guide device, which is associated with the dental arch model. This results in a three-point guiding by which a radial adjustment of the bracket support is attainable.

According to another advantageous feature the bracket support is engaged with the bracket opening. Hence, the bracket opening is used not only for receiving the orthodontic arch wire but also for retaining the bracket on the bracket support.

Further the reference element can be made detachably securable with the bracket support. Advantageously the reference element is constructed in several parts, the parts being adjustable in their relative positions.

To attain a torsion-free simple connection between the reference element and the bracket support it is advantageous that the bracket support has a cavity on its free end with a polygonal cross section which corresponds approximately to the cross section of the reference element in the associated region.

Furthermore the reference element can be formed with a protruding portion which acts as a stop for the bracket support. The protruding portion then acts as a distance maintaining element for the bracket support, which increases the manipulability and the ease of removing the supports from the adhered bracket.

An additional simple combination between the bracket support and the reference element can be attained when the bracket support is formed with a free end which sits in a recess or opening of the reference element.

When the cross section of the bracket support penetrating the opening has a polygonal shape, a torsion-free combination is attained.

Advantageously the free end of the reference element is covered by a sleeve extending over a portion of its length, which contacts on a stop formed on the reference element. This achieves an improved manipulability at the position of the tooth. For exact positioning the reference element can have polygonal cross section.

According to an additional advantageous feature the bracket support has a surface with a curvature determined by the course of the associated wire segment on its end carrying the bracket.

Advantageously the guide device is deformable in its principal plane at least approximately according to the curvature of the bite plane of the associated idealized dental arch model and can be fixed in a particular definite shape. Similarly the guide device can be deformable in its principal mirror symmetry plane at least approximately according to the curvature of the bite plane of the associated dental arch model and can be fixed in a particular configuration. Both these last-mentioned embodiments are particularly suitable for correction of extreme overbite of the front teeth of the patient, since in such a case bracket placement on the teeth is then made possible.

Advantageously the guide device is deformable in relation to its arc shape so that the curve and the inner width between the limbs of the arc are adjustable.

BRIEF DESCRIPTION OF THE DRAWING

The above and other objects, features and advantages of our invention will become more readily apparent from the following description, reference being made to the accompanying highly diagrammatic drawing in which.

SPECIFIC DESCRIPTION

Figure 1:
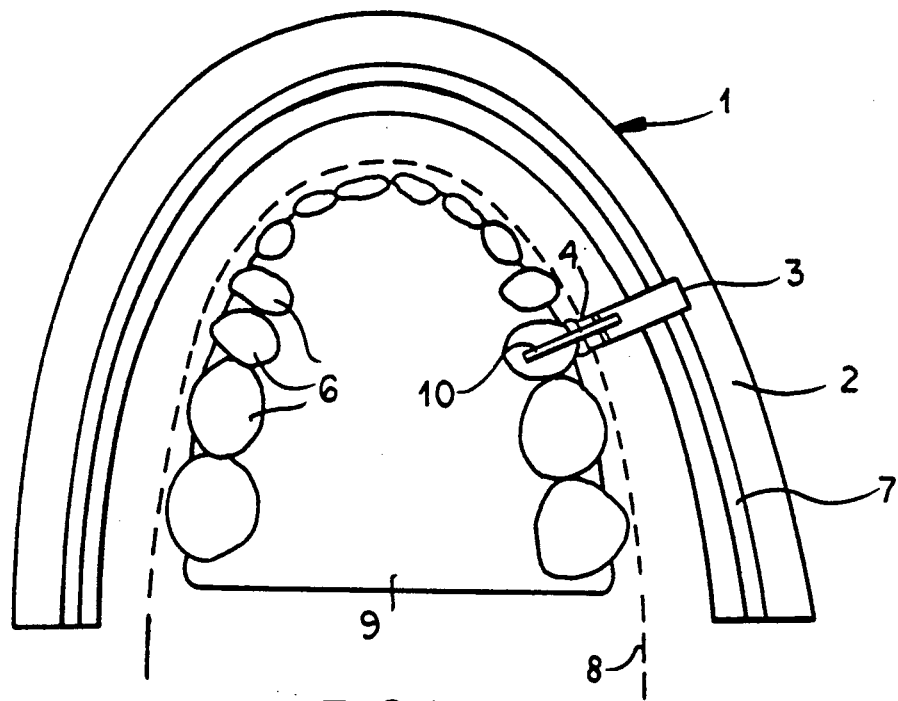
FIG. 1 is a top plan view of an orthodontic appliance according to our invention and an idealized model of the teeth.

In FIG. 1 an idealized model 9 of the teeth is shown, to which an apparatus for making an orthodontic appliance has been attached After casting the jaw of the patient a model of the teeth is made with the teeth in the erroneous positions to be corrected, which is subsequently known as a characteristic occlusal model. By separation of the tooth replicas 6 which are incorrectly oriented from each other and from the model base subsequently in a step known as "set-up", by newly arranging the tooth replicas in the therapeutically desirable ideal positions with respect to each other and to the other teeth in the opposing jaw, the so-called idealized dental arch model 9 is produced Brackets 4 with openings 5 are provided at the individual tooth replicas 6 of one such idealized dental arch model 9. The openings 5 are formed in the preponderance of cases by slots. The brackets with the openings are brought into a subsequent relative position characterized as the ideal position, which corresponds to the position in which they are mounted later on the patient's teeth. The position of all the bracket openings 5 is harmonized with the course 8 of the so-called orthodontic arch wire portions, arcs or segments.

The course 8 of the ideal wire arc is determined individually for each idealized dental arch model 9 and maintained during the treatment. The ideal arrangement of the brackets 4 in the idealized model is effected by bracket supports—however only one bracket support 3 has been shown—which are positioned on the tooth replicas 6 of the idealized dental arch model 9 by a template-like guide device 2 corresponding with the fixed ideal wire arc course 8 so that the bottoms of the openings 5 of the brackets 4 supported by the bracket supports 3 are covered by the ideal wire arc on its course or path 8. The end-face of the bracket support portion of the bracket support 3 facing the base of the bracket 5 is provided with a curvature corresponding to the ideal arc curvature directly or according to which segment of the ideal wire arc is found adjacent the bracket concerned in the treatment. Correspondingly the curvature of the end-face of the bracket supporting member 18 in the case of a canine is especially well conformed.

The apparatus used in our process is supported in a suitable way by a holder. In the embodiment shown the guide device 2 has a rail-like guide groove 7 of rectangular cross section. The guide groove 7 and the edge 7' facing the idealized dental arch model 9 run parallel to the course of the ideal wire arc 8.

Figure 2:
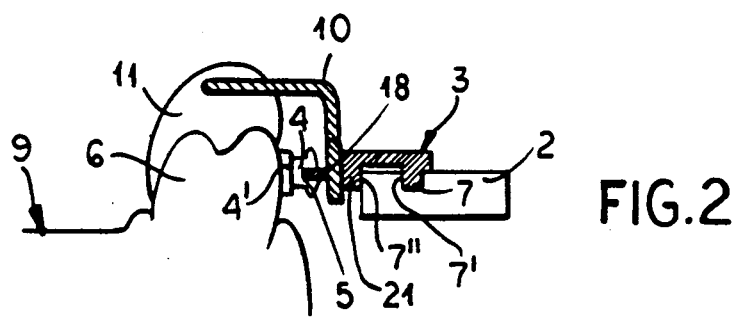
FIG. 2 is a side plan view of a first embodiment of the orthodontic appliance showing bracket supports and reference elements.
Figure 3:
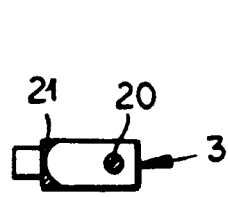
FIG. 3 is a bottom plan view of the bracket support 3 according to first embodiment illustrated in FIG. 1.
Figure 4:
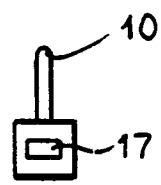
FIG. 4 is an end plan view of the first embodiment of the reference element as illustrated in FIG. 1.

A portion of the cross section of the dental arch model 9 and an embodiment of the orthodontic appliance are shown in detail in FIGS. 2 to 4.

The lower side of the bracket support 3 has a cylindrical projection 20 which engages with slight play exactly in the guide groove 7 and a protruding member 21 which fits tightly on the edges of the guide device 2 facing the idealized dental arch model 9 on mounting the bracket support 3.

The protruding member 21 is spaced from said cylindrical projection a distance which corresponds to that between a side wall 7" of the guide and an edge 7' of the guide device associated with the cylindrical projection 20.

The projection 20 and the protruding member 21 cause a continuous radial adjustment of the bracket support 3 to the course of the idealized wire arc and overlap the bracket supporting members 18 and thus the slot-like bracket openings 5 with the course of the idealized wire arc 8.

The reference element 10 connected slidable horizontally with the bracket support 3 has an opening 17 for receiving and guiding the bracket support 3 torsion-free, whereby the opening surfaces of the bracket support 3 form a stop for the motion relative to the perpendicular section of the reference element 10.

The individual reference element 10 projects with its horizontal section beyond the occlusal and incisal contour of the tooth replica 6 of the idealized dental arch model 9 and is attached to an arch-shaped negative 11 which is formed for example from a hardenable material replicating the tooth surface partially on the buccal and/or labial, occlusal and/or incisal as well as lingual part and, if necessary, is divided into portions associated with the separated tooth replica 6.

The bracket 4 is then positioned by the negative 11 individually in its ideal position on the tooth replica 6 of the idealized dental arch model 9 with its bracket base 4'. The portion with the brackets 4, the bracket supports 3 and the reference element 10 are then lifted as a stable reference unit from the tooth replica 6 and if necessary provided under the bracket base 4' with a suitable hardenable material and on again putting the bracket 4 on the tooth replica 6 the gap between the bracket base 4' and the tooth surface is filled by a compensating mass 19.

The bracket 4 thus provided with the individual compensating mass 19 is lifted from the tooth replica 6, whereby the compensating mass 19 adheres to the bracket base 4' rigidly and is transferred with the help of the negative 11 to the patient's tooth and attached there.

The slidability of the bracket support 3 relative to the reference element 10 can be used both in formation of the individual bracket base and also on gluing to the patient's tooth. Before mounting the bracket 4 on the tooth replica and/or on the patient's tooth the bracket support 3 can be pulled back somewhat from the opening 17 so that the compensating mass 19 and/or the adhesive is not stripped away on mounting and both are pressed after positioning the bracket 4 on the tooth, when the bracket support 3 is again pushed into the opening 17 of the reference element 10 until at the stop or contact. After successful attachment of the bracket 4 to the patient's tooth the bracket support 3 is again drawn from the bracket slot 5 to allow a removal of the reference element 10 and the negative.

Figure 5:
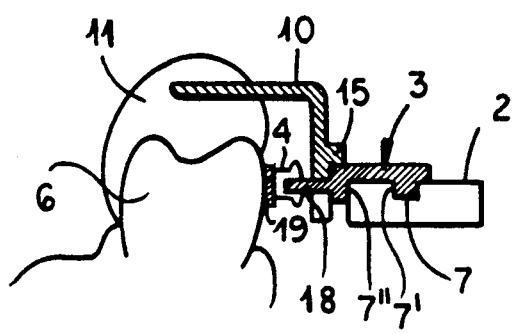
FIG. 5 is a side plan view of a second embodiment of the orthodontic appliance showing bracket supports and reference elements.
Figure 6:
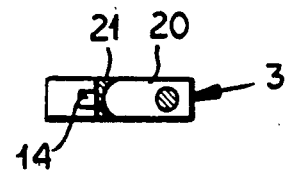
FIG. 6 is a bottom plan view of the bracket support 3 according to the second embodiment illustrated in FIG. 5.
Figure 7:
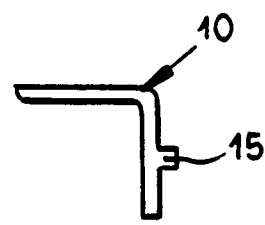
FIG. 7 is a side plan view of the reference element of the second embodiment as illustrated in FIG. 5.

The configuration of the bracket support 3 relative to the reference element 10 can be such, as shown from FIGS. 5 to 7, that the reference element 10 provided with a protruding portion 15 can be drawn from an opening 14 of the bracket support 3 formed as a torsion-free guide.

Figure 8:
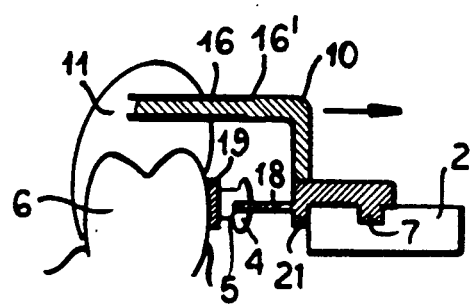
FIG. 8 is a side plan view of a third embodiment of the orthodontic appliance showing a bracket support and a horizontally slidable reference element.

However, as shown in FIG. 8, the bracket support 3 and the reference piece 10 can be made from a single piece and is slidable with a stop 16' in a polygonal sleeve 16 acting as a torsion-free guide. The sleeve 16 is attached with the negative 11.

Figure 9:
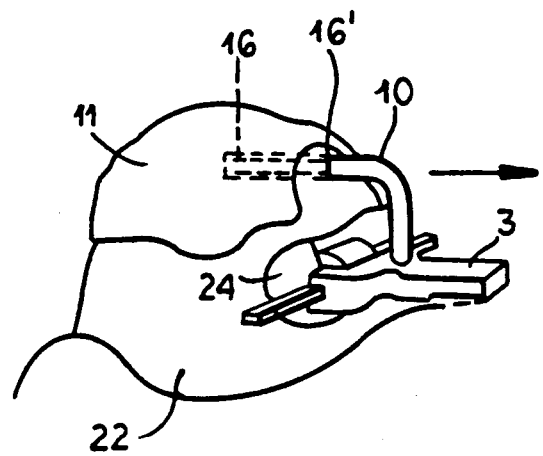
FIG. 9 is a perspective view of a bracket support for brackets formed as molar tubes with a special structure for the reference element

FIG. 9 shows a perspective view of a reference unit on a patient's tooth 22, with a support 3 formed analogously to the bracket support 3 in FIG. 8 for positioning and carrying of buccal tubes 24, which indirectly positions the tube to the patient's tooth 22 by a wire with a square section filling almost completely the interior of the buccal tube. The reference part 10 is held by a sleeve 16 with stop 16' in a portion of the negative 11.

The process for making an individualized bracket base can be varied, since the compensating layer between the bracket located ideally on the tooth and the tooth surface is not formed directly on the model but directly by the adhesive on positioning the bracket on the patient's tooth.

The apparatus designed for carrying out the process according to our invention can be equipped with a set of various guide devices according to different jaw formations or shapes.

The basic process of our invention and the apparatus can vary in many ways from the above-described embodiments without varying from the basic idea and the scope of our invention. Also our invention is equally useful for brackets attached to the buccal surfaces of teeth as well as for ones attached to the lingual surfaces of teeth. Moreover the invention can be used in connection with specially structured brackets, e.g. molar tubes.

By the "guide" in the following claims we mean a portion of the guide device, in particular here in this embodiment the rail 7.

I claim:

1. In a process for making an orthodontic appliance for a dental arch of a patient having a plurality of individual teeth, which appliance correctly positions said teeth of said patient, said orthodontic appliance comprising
a plurality of brackets having openings and being correlated with said individual teeth and
an orthodontic arch wire attachable to said brackets, the steps of said process comprising making a characteristic occlusal model of said dental arch of said patient,
dividing said occlusal model into a plurality of individual tooth replicas,
making an idealized model of said dental arch by arrangement of said individual tooth replicas into a plurality of corrected positions and fixing a guide device and said idealized model in relation to each other,
providing a respective bracket support guided on said guide device for each of said brackets corresponding to respective tooth replicas,
adjusting and setting said brackets in a desired position in relation to the respective tooth replicas by said bracket supports so that a plurality of bottoms of said openings of said brackets nest to each other lie along a line which forms an at least segmentwise continuously running curve which follows an idealized course of the edge of said orthodontic arch wire opposite to said dental arch in the region of incisal edges and/or occlusal surfaces of said tooth replicas
making at least one negative extending over at least one of said tooth replicas, which negative covers at least a portion of the clinical crown of the respective tooth replica, from a hardenable material and connecting and combining said negative with a respective reference element projecting from each of said bracket supports to form together with each respective bracket and bracket support a respective reference unit for the respective tooth replica,
separating said reference units from said tooth replicas and from said guide device
if necessary
dividing said negative into portions each associated with a respective one of said tooth replicas,
providing a hardenable compensating mass as required on the surfaces of said brackets correlated with the surfaces of said teeth for filling an intervening space resulting from the positioning of said brackets and
again setting said reference units with said hardenable compensating mass on said tooth replicas for casting,
thereafter installing said reference units on the appropriate teeth in said dental arch of said patient,
fixing said brackets on said teeth and removing said reference units without said brackets, and
installing said orthodontic arch wire in said openings of said brackets.

2. The process defined in claim 1 wherein said filling of said intervening space with said compensating mass is effected by injecting.

3. The process defined in claim 1 wherein said negative for all of said tooth replicas of said dental arch is made in a single piece.

4. The process defined in claim 1 wherein said negative is positioned on said teeth of said patient before securing said brackets to said teeth.

5. The process defined in claim 1 wherein said negative is made by applying a first layer of said hardenable material to said tooth replicas and bonding said reference elements in said negative by applying a second layer of said hardenable material to said first layer.

6. The process defined in claim 1 wherein said brackets are fixed to said dental arch by adhesive.

7. In an apparatus for making an orthodontic appliance from a plurality of brackets and an orthodontic arch wire, the apparatus comprising
a guide device and
a plurality of bracket supports mounted movable on said guide device, the improvement wherein
said guide device has a guide for said bracket supports formed with a pair of parallel edges running substantially parallel to an ideal course of said orthodontic arch wire, said guide being formed to slidably receive said bracket supports,
each bracket support is unitarily formed with a pair of parts respectively engaging the edges and maintaining the respective support substantially perpendicular to the edges at the location where they engage the parts, and
said bracket supports are each provided with a reference element and are each combinable with a respective one of the brackets, each reference element being L-shaped with a protruding portion vertical to a plane of said bracket support and a leg portion above and perpendicular to said protruding portion and pointed toward said arch wire and parallel to said plane.

8. The improvement defined in claim 7 wherein each of said reference elements and the respective bracket supports are adjustable in position relative to each other.

9. The improvement defined in claim 7 wherein said guide is formed from a rail on which said bracket supports are mounted slidably.

10. The improvement defined in claim 7 wherein said bracket supports are engaged in openings of the respective brackets.

11. The improvement defined in claim 7 wherein each reference element is detachably securable with the respective bracket support.

12. The improvement defined in claim 7 wherein each reference element comprises a plurality of parts that are adjustable in position relative to each other.

13. The improvement defined in claim 7 wherein each bracket support has a cavity in a free end thereof with a polygonal cross section which corresponds approximately to that of the respective reference element in the associated region.

14. The improvement defined in claim 14 wherein the protruding portion of each reference element serves as a stop for the respective bracket support.

15. The improvement defined in claim 7 wherein each bracket support is formed with a free end which engages in a corresponding cavity of the respective reference element.

16. The improvement defined in claim 15 wherein a portion of each bracket support penetrating the respective cavity has a polygonal cross section.

17. The improvement defined in claim 7 wherein a free end of each reference element is covered by a sleeve extending longitudinally over the respective leg portion of said reference element and engageable with a stop portion on said leg portion.

18. The improvement defined in claim 7 wherein each reference element has a polygonal cross section.

19. The improvement defined in claim 7 wherein said guide device is at least partially deformable and fixable in a principal plane at least approximately corresponding to a curvature of a jaw plane of an associated idealized model of said ideal course.

20. The improvement defined in claim 7 wherein said guide device is deformable and fixable in a principal mirror image plane at least approximately corresponding to as curvature of a jaw plane of an associated idealized model of said ideal course.

21. The improvement defined in claim 7 wherein said guide device is deformable relative to an archlike course, a curvature and an inner width between extreme portions of said archlike course being adjustable.

22. The improvement defined in claim 7 wherein the parts of the bracket supports each include a cylindrical projection and a protruding member.

23. In an apparatus for making an orthodontic appliance from a plurality of brackets and an orthodontic arch wire, the apparatus comprising
a guide and
a plurality of bracket supports mounted movable on said guide,
the improvement wherein
said guide device has a guide for said bracket supports running substantially parallel to an ideal course of said orthodontic arch wire, said guide being formed to receive said bracket supports,
said bracket supports are each provided with a reference element and are each combinable with a respective bracket, each reference element being L-shaped with a protruding portion vertical to a plane of said bracket support and a leg portion above and perpendicular to said protruding portion pointed toward said arch wire and parallel to said plane, and
each bracket support has
a cylindrical projection by which it is slidable in said guide and
an additional protruding member which is formed unitarily in said support and which is spaced from said cylindrical projection a distance which corresponds to that between a side wall of said guide and an edge of said guide device associated with said cylindrical projection.

24. In an apparatus for making an orthodontic appliance from a plurality of brackets and orthodontic arch wire, the apparatus comprising
a guide and
a plurality of bracket supports mounted movable on said guide,
the improvement wherein
said guide device has a guide for said bracket supports running substantially parallel to an ideal course of said orthodontic arch wire, said guide being formed to receive said bracket supports,
said bracket supports are each provided with a reference element and are each combinable with a respective bracket, each reference element being L-shaped with a protruding portion vertical to a plane of said bracket support and a leg portion above and perpendicular to said protruding portion pointed toward said arch wire and parallel to said plane, and
an end face of each bracket support engageable with the respective bracket has a curved surface whose curvature corresponds to the course of an associated part of said orthodontic arch wire.

* * * * *